United States Patent [19]

Shaffer et al.

[11] Patent Number: 5,092,347

[45] Date of Patent: Mar. 3, 1992

[54] PERSONALIZED SOCK KIT FOR RELIEVING FOOT AND ANKLE PAIN

[76] Inventors: David E. Shaffer, 386 Spruce La., East Meadow, N.Y. 11554; Michael P. Della Corte, 283 Carnation Ave, Floral Park, N.Y. 11001

[21] Appl. No.: 495,413

[22] Filed: Mar. 19, 1990

[51] Int. Cl.⁵ .............................................. A61K 5/14
[52] U.S. Cl. .................................. 128/892; 128/893; 128/894; 36/143
[58] Field of Search ................ 128/581, 582, 80 R, 128/882, 893, 894

[56] References Cited

U.S. PATENT DOCUMENTS

| | | |
|---|---|---|
| 847,311 | 3/1907 | Bronnenkant ................. 128/894 |
| 3,119,390 | 1/1964 | Levitt .......................... 128/894 |
| 3,253,591 | 5/1966 | Scholl .......................... 128/894 |
| 3,301,254 | 1/1967 | Schickedanz ................ 128/894 |
| 3,407,406 | 10/1968 | Werner et al. ............... 128/893 X |
| 4,926,568 | 5/1990 | Coffman ...................... 128/582 X |

FOREIGN PATENT DOCUMENTS 212073 12/1957 Australia ........................... 128/893

Primary Examiner—Robert A. Hafer
Assistant Examiner—Kerry Owens
Attorney, Agent, or Firm—Michael I. Kroll

[57] ABSTRACT

A personalized sock self made by a patient for relief of foot discomfort and which includes a plurality of corrective components each having a shape formed for a specific correction, a sock which has a surface that contains a plurality of shapes each disposed for a specific correction and each shape of the plurality of shapes that are contained on the surface of the sock are substantially component of the plurality of corrective components, hooks and loops for affixing the plurality of corrective components to the surface of the sock so as to allow the patient to modify the sock by affixing a corrective component for the specific correction of the plurality of corrective components to a substantially equivalent shape of the plurality of shapes that are contained on the surface of the sock so that a personalized sock can be self made by the patient for the relief of foot discomfort.

27 Claims, 2 Drawing Sheets

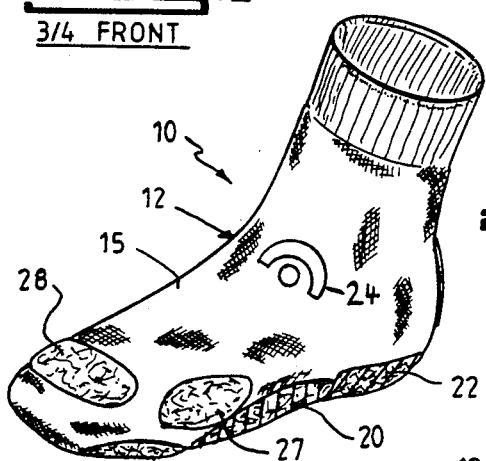
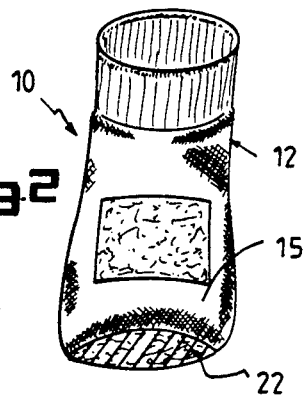
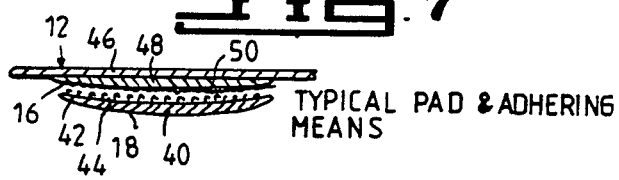
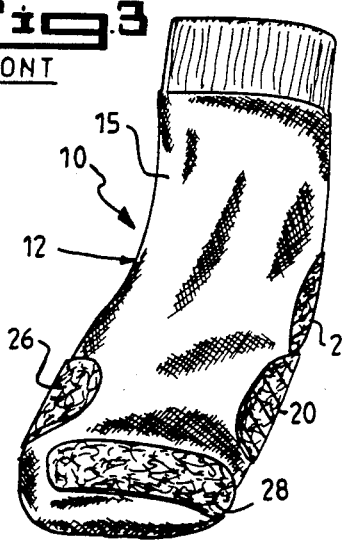
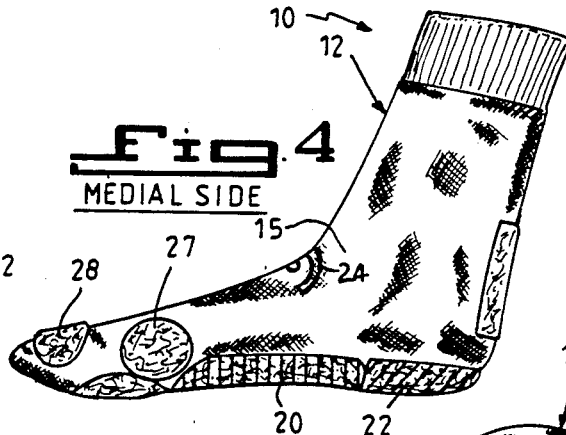
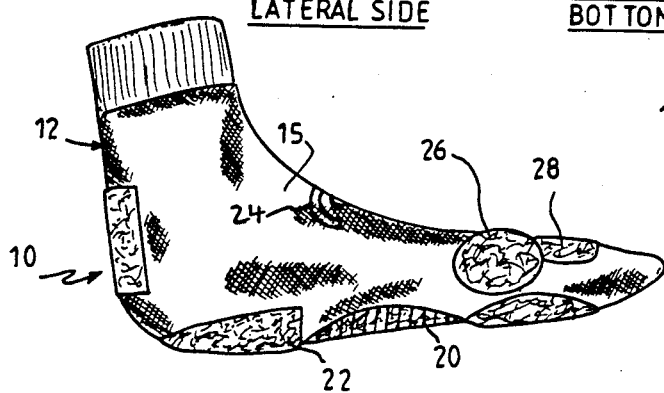
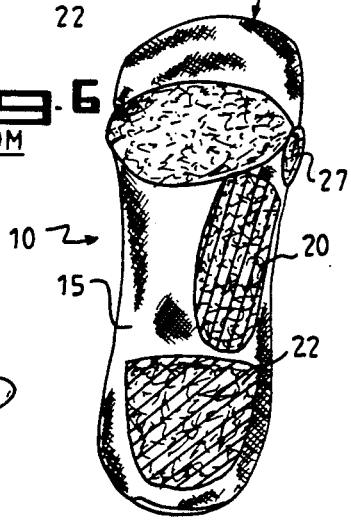

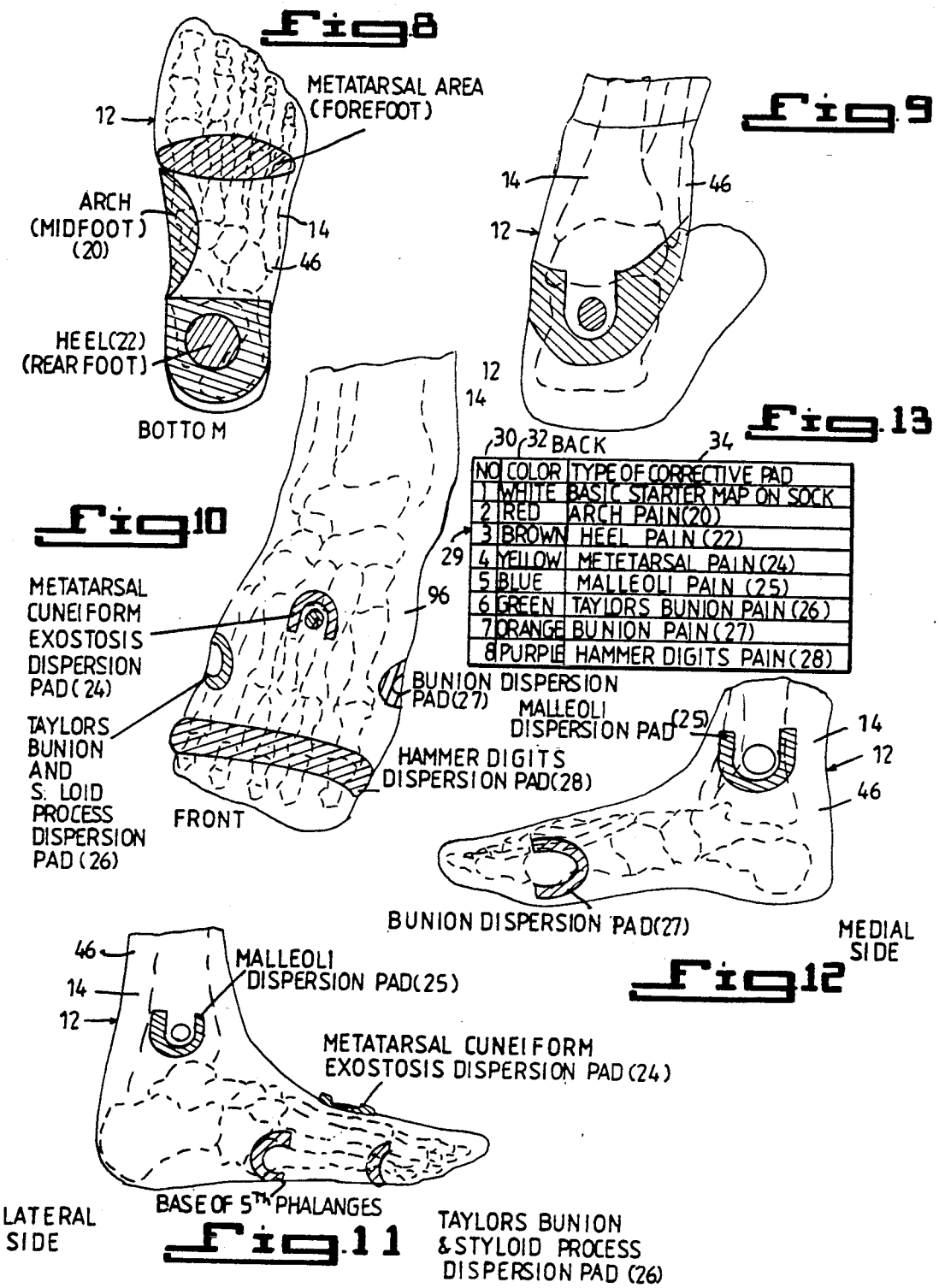

PERSONALIZED SOCK KIT FOR RELIEVING FOOT AND ANKLE PAIN

BACKGROUND OF THE INVENTION

1. Field of the Invention

The present invention relates to an orthotic device. More particularly, the present invention relates to an orthotic device which relieves the pain caused by deformities of the foot by using a plurality of specific paddings that self adhere to specific mapped out areas on an unique sock.

2. Description of the Prior Art

Orthotic devices or insoles are generally inserted into shoes and are made to accommodate or relieve pain on the bottom of the foot. They cannot function properly without the use of shoes. Existing functional or accommodative orthotics ca be affixed to the personalized sock kit for relieving foot and ankle pain by either adhesives or velcro, allowing use of these devices without shoe gear. Previously, orthotics could only be used enclosed in shoes. Existing or adjustable gait plates can also be affixed to the sock of the present invention.

The boom in jogging and running, that has characterized the fitness movement, has increased the demand for orthotic devices. The prior art orthotic devices are expensive, apply only to specific corrections if corrections are provided, require the services of a professional to construct and fit, and cannot be personalized by the patient.

Numerous innovations for kits for relieving foot and ankle pain have been provided in the prior art that are adapted to be used. Even though these innovations may be suitable for the specific individual purposes to which they address, they would not be suitable for the purposes of the present invention as heretofore described.

SUMMARY OF THE INVENTION

Accordingly, it is an object of the present invention to provide a sock kit for relieving foot and ankle pain which avoids the disadvantages of the prior art.

More particularly, it is an object of the present invention to provide a personalized sock kit for relieving foot and ankle pain which can be self made by the patient, offers an easy and affordable way of relieving foot discomfort of a patient, is coded to allow the patient to customize the sock for specific corrections, is inexpensive, and is adjustable.

The combination of the unique sock with self adhering pads that together function as an orthotic offers a new approach for relieving foot pain with or without the use of shoes. There are numerous applications in health care and athletics. The present invention allow the wearer to make all the adjustments and placements of the pads at the area where there is pain.

The personalized sock kit for relieving foot and ankle pain of the present invention to the combination of Shaffer et al. U.S. Pat. No. 4,841,648 for a personalized insole kit and Shaffer et al. U.S. Pat. No. 4,856,505 for an apparatus for relieving pain and discomfort of a bunion.

The present invention is a unique combination of a sock and a plurality of accommodative components that are easy to use and do not require instructions from a Physician/Podiatrist; relieves painful deformities not only on the bottom of the foot, but also on the sides, the top, the ankle, and the lower leg; can be worn with or without shoes, or in sandles; includes a unique mapping system provided on the sock which matches a plurality of corresponding coded pads which are self adhering and easily applied by the individual wearing the sock, the pads, and the mapping system can be on the inside or the outside of the sock; can be worn in women's high heels, boots, and sandles (there are very few orthotic devices that can be worn in women's shoes due to the materials and bulk of the devices); can relieve pain and pressure caused by bunions by the use of dispersion padding; can relieve pain and pressure caused by hammer toes which are deformities located on the top of the toes aside from pads that adhere to the skin, no other device, that can be worn in the shoe, can relieve pain caused by hammer toes; can relieve pain caused by bone spurs at the instep on the top of the foot; can relieve pain and pressure from pump bumps which are bone spurs on the back of the heel; can relieve pain from heel spurs; can relieve arch pain; can relieve metatarsal pain in the ball of the foot; can relieve pain from Tailor's bunions which are bumps on the outer side of the foot; there is no special casting or fabrication, the sock is placed on the foot and the self adhering pads are applied to the coded areas where needed, the user is not limited to self adhering materials, i.e. hooks and loops, snaps, glue, etc., there is no limitation to any materials; the pads are replaceable when they wear out; can be used by athletes for pain relief by the use of dispersion padding applied to the sock; and there is no adhesive applied to the skin so that it can be used by people with poor circulation, diabetes, and people allergic to tape.

There are other socks available for comfort and for use by diabetics, however pain is relieved by the use of different weaves and sock thicknesses with the use of fixed components whereas the present invention is adjustable to the wearer's individual needs and is user friendly.

In keeping with these objects, and with others which will become apparent hereinafter, one feature of the present invention resides, briefly stated, in a personalized sock kit for relieving foot and ankle pain and which is self made by a patient for relief of foot and ankle discomfort and which includes a plurality of corrective components each having a shape formed for a specific correction, a sock, and means for affixing the plurality of corrective components to the surface of the sock so as to allow the patient to modify the sock by affixing a corrective component for the specific correction of the plurality of corrective components to the surface of the sock wherein the sock has inner and outer surfaces containing a plurality of shapes each disposed for the specific correction and each shape of the plurality of shapes contained on the inner and outer surfaces of the sock are substantially equivalent to a respective shape of a corrective component of the plurality of corrective components.

When the personalized sock kit for relieving foot and ankle pain is designed in accordance with the present invention, a personalized sock can be self made by the patient for the relief of foot discomfort.

In accordance with another feature of the present invention, the sock and the each corrective component of the plurality of corrective components is a resilient material.

Another feature of the present invention is that the sock and the each corrective component of the plurality of corrective components is foam pad.

Yet another feature of the present invention is that the plurality of corrective components is not limited to seven.

Still another feature of the present invention is that a first corrective component of the seven corrective components is an arch pad.

Yet still another feature of the present invention is that a second corrective component of the seven corrective components is a heel pad.

Still yet another feature of the present invention is that a third corrective component of the seven corrective components is a metatarsal cuneiform exostosis dispersion pad.

Another feature of the present invention is that a fourth corrective component of the seven corrective components is a malleoli dispersion.

Yet another feature of the present invention is that a fifth corrective component of the seven corrective components is Taylor's bunion dispersion pad.

Still another feature of the present invention is that a sixth corrective component of the seven corrective components is a bunion dispersion pad.

Yet still another feature of the present invention is that a seventh corrective component of the seven corrective components is a hammer digits dispersion pad.

Still yet another feature of the present invention is that the each corrective component of the plurality of corrective components is color coded to the substantially equivalent shape of the plurality of shapes disposed on the surface of the sock.

Another feature of the present invention is that a first corrective component of the seven corrective components is colored red.

Yet another feature of the present invention is that a second corrective component of the seven corrective components is colored brown.

Still another feature of the present invention is that a third corrective component of the seven corrective components is colored yellow.

Yet still another feature of the present invention is that a fourth corrective component of the seven corrective components is colored blue.

Still yet another feature of the present invention is that a fifth corrective component of the seven corrective components is colored green.

Another feature of the present invention is that a sixth corrective component of the seven corrective components is colored orange.

Yet another feature of the present invention is that a seventh corrective component is colored purple.

Still another feature of the present invention is that the each corrective component of the plurality of corrective components is numerically coded to the substantially equivalent shape of the plurality of shapes disposed on the surface of the sock.

Yet still another feature of the present invention is that a first corrective component of the seven corrective components is numbered two.

Still yet another feature of the present invention is that a second corrective component of the seven corrective components is numbered three.

Another feature of the present invention is that a third corrective component of the seven corrective components is numbered four.

Yet another feature of the present invention is that a fourth corrective component of the seven corrective components is numbered five.

Still another feature of the present invention is that a fifth corrective component of the seven corrective components is numbered six.

Yet still another feature of the present invention is that a sixth corrective component of the seven corrective components is numbered seven.

Still yet another feature of the present invention is that a seventh corrective component of the seven corrective component is numbered eight.

Another feature of the present invention is that the affixing means include hooks and loops.

Yet another feature of the present invention is that it further comprises a code chart separate from the sock and for further assisting the patient in properly positioning the plurality of corrective components.

The novel features which are considered characteristic for the invention are set forth in particular in the appended claims. The invention itself, however, both as to its construction and its method of operation, together with additional objects and advantages thereof, will be best understood from the following description of the specific embodiment when read in connection with the accompanying drawing.

BRIEF DESCRIPTION OF THE DRAWING

FIG. 1 is a perspective three-quarter front view of the sock of the present invention with six visible corrective components disposed on the outer surface of the sock;

FIG. 2 is a perspective back view of the sock of the present invention with two visible corrective components disposed on the outer surface of the sock;

FIG. 3 is a perspective front view of the sock of the present invention with four visible corrective components disposed on the outer surface of the sock;

FIG. 4 is a perspective medial view of the sock of the present invention with six visible corrective components disposed on the outer surface of the sock;

FIG. 5 is a perspective lateral side view of the sock of the present invention with six visible corrective components disposed on the outer surface of the sock;

FIG. 6 is a perspective bottom view of the sock of the present invention with five visible corrective components disposed on the outer surface of the sock;

FIG. 7 is a cross sectional view of a typical corrective component being attached to the sock of the present invention by the use of VELCRO ® as the adhering means;

FIG. 8 is a bottom view of the sock of the present invention with three corrective components disposed on the inner surface of the sock bottom, with the foot shown in phantom;

FIG. 9 is a perspective back view of the sock of the present invention with one corrective component disposed on the inner surface of the sock back, with the foot shown in phantom;

FIG. 10 is a perspective front view of sock of the present invention with three corrective components disposed on the inner surface of the sock front, with the foot shown in phantom;

FIG. 11 is a lateral side view of the sock of the present invention with two corrective components disposed on the inner surface of the sock lateral side, with the foot shown in phantom; and FIG. 12 is a medial side view of the sock of the present invention with two corrective components disposed on the inner surface of the sock medial side, with the foot shown in phantom.

FIG. 13 is a chart describing the type of each corrective pad along with its corresponding number and color.

LIST OF REFERENCE NUMERALS

10—personalized sock kit for relieving foot and ankle pain

12—sock of the personalized sock kit for relieving foot and ankle pain 10

14—inner surface of the sock 12

15—outer surface of the sock 12

16—plurality of strategically disposed two dimensional shapes that form the maps on the inner surface 14 and the outer surface 15

18—plurality of corrective components of the personalized sock kit for relieving foot and ankle pain 10

20—arch pad of the plurality of corrective components 18

22—heel pad of the plurality of corrective components 18

24—metatarsal cuneiform exostosis dispersion pad of the plurality of corrective components 18

25—malleoli dispersion pad of the plurality of corrective components 18

26—Taylor's bunion dispersion pad of the plurality of corrective components 18

27—bunion dispersion pad of the plurality of corrective components 18

28—hammer digits dispersion pad of the plurality of corrective components 18

29—code chart for the personalized sock kit for relieving foot and ankle pain 10

30—number code column

32—color code column

34—correction diagnosis column

40—resilient material of the plurality of corrective components 18

42—backing of the plurality of corrective components 18

44—hook portion on the backing 42

46—material of the sock 12

48—backing

50—loop part

DETAILED DESCRIPTION OF THE PREFERRED EMBODIMENT

Referring now to the FIGURES, the personalized sock kit for relieving foot and ankle pain of the present invention is shown generally at 10. The personalized sock kit for relieving foot and ankle pain 10 includes a sock pad 12 which has an inner surface 14 and outer surface 15 that each contain a plurality of strategically disposed shapes 16. The personalized sock kit for relieving foot and ankle pain 10 also includes a plurality of corrective components 18.

The plurality of shapes 16 that are strategically disposed on the inner surface 14 and the outer surface 15 of the sock 12 provide a unique "mapping system", as shown in the FIGURES, that allows a patient to properly position the plurality of corrective components 18 for specific corrections and produce a self made personalized orthotic device.

As shown in the FIGURES, the plurality of corrective components 18 include an arch pad 20, a heel pad 22, a metatarsal cuneiform exostosis dispersion pad 24, malleoli dispersion pad 25, Taylor's bunion styloid process dispersion pad 26, bunion dispersion pad 27, hammer digits dispersion pad 28. The plurality of corrective components 18 are coded to the plurality of shapes 16 that are strategically disposed on the inner surface 14 and the outer surface 15 of the sock 12. This coding assists the patient in properly positioning the plurality of corrective components 18 for specific corrections. Either a color code or a number code or both can be used.

As shown in the FIGURES, the arch pad 20 is colored red and contains the number two. The heel pad 22 is colored brown and contains the number three. The metatarsal pad 24 is colored yellow and contains the number four.

The metatarsal cuneiform exostosis dispersion pad 25 is colored yellow and contains the number 5. The Taylor's bunion dispersion pad 26 is colored green and contains the number 6. The bunion dispersion pad 27 is colored orange and contains the number 7. The hammer digit dispersion pad 28 is colored purple and contains the number 8.

As shown in the FIGURES, the strategically disposed shape on the outer surface 15 of the sock 12, for the proper position of the arch pad 20, is colored red and contains the number two. The strategically disposed shape on the outer surface 15 of the sock 12, for the proper position of the heel pad 22, is colored brown and contains the number three. The strategically disposed shape on the outer surface 15 of the sock 12, for the proper position of the metatarsal cuneiform exostosis dispersion pad 24, is colored yellow and contains the number four. The strategically disposed shape on the outer surface 15 of the sock 12, for the proper position of the malleoli dispersion pad 25, is colored blue and contains the number five.

The strategically disposed shape on the outer surface 15 of the sock 12, for the proper position of the Taylor's bunion dispersion pad 26 is colored green and contains the number six. The strategically disposed shape on the outer surface 15 of the sock 12, for the proper position of the bunion dispersion pad 27 is colored orange and contains the number 7. The strategically disposed shape on the outer surface 15 of the sock 12, for the proper position of the hammer digits dispersion pad 28 is colored purple and contains the number 8.

To further assist the patient in properly positioning the plurality of corrective components 18 for specific corrections, a code chart 29, shown in FIG. 13, is provided. The code chart 29 includes a number code column 30, a color code column 32, and a correction diagnosis column 34. To utilize the code chart 29, the patient first looks down the correction diagnosis column 34 and locates the specific disorder. After the specific disorder has been located in the correction diagnosis column 34, the patient is then able to identify the specific number code and color code for the required correction component. Since the plurality of shapes 16 that are strategically disposed on the surface 14 of the sock pad 12 are coded to the plurality of corrective components 18, the patient, once the required corrective component is identified from the code chart 29, will know exactly where to place the required corrective component.

As shown in the FIGURES, the arch pad 20, like the heel pad 22, the metatarsal cuneiform exostosis dispersion pad 24, the malleoli dispersion pad 25, the Taylor's bunion dispersion pad 26, the bunion dispersion pad 27, and the hammer digit dispersion pad 28 are made of a resilient material 40, but is not limited to it, mounted on a backing 42 which contains a hook part 44 of a hook and loop connector. The resilient material, but is not limited to it may be foam padding but is not limited to it. The sock pad 12 is made of a sock material 46, but is not limited to it mounted on a backing 48. The outer surface 15 and the inner surface 14 of the sock 12 contains a loop part 50 of a hook and loop connector. The hook part 44 on the plurality of corrective components 18 and the loop part 50 on the sock 12 allow the plurality of corrective components 18 to be removably mounted to the sock 12. Other alternate adhering means may be used to fasten the plurality of corrective components 18 to the sock 12.

The personalized sock kit for relieving foot and ankle pain 10 of the present invention teaches the use of a sock 12 with a unique "mapping system" on the outer surface 15 and the inner surface 14 of the sock 12. The "mapping system" includes either a color code or a number code or a label for the specific type of foot discomfort. The plurality of corrective components 18 can be placed in specific areas of pain, as indicated by the "mapping system" on the outer surface 15 and the inner surface 14 of the sock 12.

By using the "mapping system", the patient can easily, affordably, and immediately relieve foot discomfort since the "mapping system" shows the required corrections. Additional corrections can be easily added when basic corrections are ineffective or inadequate.

The personalized sock kit for relieving foot and ankle pain 10 of the present invention allows the patient who cannot tolerate prescription orthotics or afford them to construct a required orthotic device by merely adjusting the sock 12 with the plurality of corrective components 18, according to the individual needs.

It will be understood that each of the elements described above, or two or more together, may also find a useful application in other types of constructions differing from the type described above.

While the invention has been illustrated and described as embodied in a personalized sock kit for relieving foot and ankle pain, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A personalized removable sock self made from simple construction by a patient for relief of foot discomfort, comprising:
   a) a plurality of removable and replaceable corrective components each having a shape formed for a specific correction so that the patient's money is saved because only said plurality of corrective components would need replacement, said sock and said each corrective component of said plurality of corrective components is a foam pad;
   b) said removable sock having a surface containing a plurality of two-dimensional shapes forming a map in which each shape of said plurality of two-dimensional shapes being disposed for said specific correction, void of the use of an elastic band to hold said plurality of removable and replaceable corrective components directly to the foot so that the body portion of the device may receive shoe pressure from the affliction and transfer that pressure to healthy tissue there around, each shape of said plurality of two-dimensional shapes contained on said surface of said sock being substantially equivalent to a respective shape of a corrective component of said plurality of corrective components, said sock and said each corrective component of said plurality of corrective components is a foam pad, said plurality of components being affixed to said sock as needed and said sock is kept in a shoe, such that said sock should not get dirty;
   c) means for self adhering said plurality of corrective components in a simple fashion to said surface of said sock so as to allow the patient to modify said sock by self adhering a corrective component for said specific correction of said plurality of corrective components to a substantially equivalent shape of said plurality of two-dimensional shapes contained on said surface of said sock so that a personalized removable sock can be self made from simple construction by the patient for the relief of foot discomfort.

2. A sock as defined in claim 1, wherein said sock and said each corrective component of said plurality of corrective components is a resilient material.

3. A sock as defined in claim 2, wherein a first corrective component of said plurality of corrective components is an arch pad.

4. A sock as defined in claim 2, wherein a second corrective component of said plurality of corrective components is a heel pad.

5. A sock as defined in claim 2, wherein a third corrective component of said plurality of corrective components is a metatarsal cuneiform exostosis dispersion pad.

6. A sock as defined in claim 2, wherein a fourth corrective component of said plurality of corrective components is a malleoli dispersion.

7. A sock as defined in claim 2, wherein a fifth corrective component of said plurality of corrective components is Taylor's bunion dispersion pad.

8. A sock as defined in claim 2, wherein a sixth corrective component of said plurality of corrective components is a bunion dispersion pad.

9. A sock as defined in claim 2, wherein a seventh corrective component of said plurality of corrective components is a hammer digits dispersion pad.

10. A sock as defined in claim 2, wherein said each corrective component of said plurality of corrective components is color coded to said substantially equivalent shape of said plurality of shapes disposed on said surface of said sock.

11. A sock as defined in claim 10, wherein a first corrective component of said plurality of corrective components is colored red.

12. A sock as defined in claim 10, wherein a second corrective component of said plurality of corrective components is colored brown.

13. A sock as defined in claim 10, wherein a third corrective component of said plurality of corrective components is colored yellow.

14. A sock as defined in claim 10, wherein a fourth corrective component of said seven corrective components is colored blue.

15. A sock as defined in claim 10, wherein a fifth corrective component of said plurality corrective components is colored green.

16. A sock as defined in claim 10, wherein a sixth corrective component of said plurality of corrective components is colored orange.

17. A sock as defined in claim 10, wherein a seventh corrective component is colored purple.

18. A sock as defined in claim 2, wherein said each corrective component of said plurality of corrective components is numerically coded to said substantially equivalent shape of said plurality of shapes disposed on said surface of said sock.

19. A sock as defined in claim 18, wherein a first corrective component of said plurality of corrective components is numbered two.

20. A sock as defined in claim 18, wherein a second corrective component of said plurality of corrective components is numbered three.

21. A sock as defined in claim 18, wherein a third corrective component of said plurality of corrective components is numbered four.

22. A sock as defined in claim 18, wherein a fourth corrective component of said plurality of corrective components is numbered five.

23. A sock as defined in claim 18, wherein a fifth corrective component of said plurality of corrective components is numbered six.

24. A sock as defined in claim 18, wherein a sixth corrective component of said plurality of corrective components is numbered seven.

25. A sock as defined in claim 18, wherein a plurality of the corrective component of said plurality of corrective component is numbered eight.

26. A sock as defined in claim 1, wherein said affixing means include hooks and loops.

27. A sock as defined in claim 1; further comprising a code chart separate from the sock and for further assisting the patient in properly positioning said plurality of corrective components.

* * * * *